United States Patent [19]

Masson et al.

[11] 4,138,213

[45] Feb. 6, 1979

[54] AGGLUTINATION IMMUNOASSAY OF IMMUNE COMPLEX WITH RF OR Clq

[75] Inventors: Pierre L. Masson, Brussels, Belgium; Joseph Heremans, deceased, late of Leuven, Belgium, by Marie-Thérèse Bracke Heremans, legal representative

[73] Assignee: Technicon Instruments Corporation, Tarrytown, N.Y.

[21] Appl. No.: 799,116

[22] Filed: May 20, 1977

Related U.S. Application Data

[63] Continuation-in-part of Ser. No. 578,698, May 19, 1975, Pat. No. 4,062,935.

[30] Foreign Application Priority Data

May 20, 1974 [GB] United Kingdom ............... 22377/74

[51] Int. Cl.² ..................... G01N 31/14; G01N 33/16
[52] U.S. Cl. ................................ 23/230 B; 23/230.6; 195/103.5 A; 424/1; 424/8; 424/12
[58] Field of Search ....................... 424/12; 23/230 B; 195/103.5 A

[56] References Cited

U.S. PATENT DOCUMENTS

3,658,982  4/1972  Reiss ..................................... 424/12
3,689,632  9/1972  Mizushima ............................. 424/12

OTHER PUBLICATIONS

J. S. Cowdery, Jr., J. Immunology, 114 (1), 5-9 (1975).
U. E. Nydegger, J. Clin. Invest., 54, 297-309 (1974).
Chemical Abstracts, 74: 2303c (1971).
Chemical Abstracts, 81: 36322t (1974).

Primary Examiner—Sidney Marantz
Attorney, Agent, or Firm—S. P. Tedesco; Eric P. Schellin

[57] ABSTRACT

A method of determining Ab:Ag complex in a biological fluid sample comprising adding to the sample a solution of RF or Clq and a known quantity of a material, such as immunoglobulin-coated polystyrene particles, which is caused to agglutinate on contact with RF or Clq, and detecting the amount of material which is not agglutinated.

12 Claims, 5 Drawing Figures

AGGLUTINATION IMMUNOASSAY OF IMMUNE COMPLEX WITH RF OR Clq

BACKGROUND OF THE INVENTION

This is a continuation-in-part of Ser. No. 578,698, filed May 19, 1975, Masson et al., U.S. Pat. No. 4,062,935 for Immunoassay Involving the Bonding of RF to the Antigen-Antibody Complex.

The present invention is concerned with the analysis of biological fluids such as urine or serum for the qualitative and quantitative determination of antibodies, antigens, and antibody:antigen complexes.

As is well known, it is important to be able to analyze biological fluids for Ab, Ag, and Ab:Ag complexes. Many diseases are characterized by the presence in body fluids such as urine and serum of Ab:Ag complexes. The Ag may comprise any of a number of different proteins, including those due to the presence of bacteria or viruses or those released from human tissues or cancer cells. The Ab are, of course, specific to the particular Ag and are predominantly immunoglobulins of the IgG class synthesized by the subject's lymphoid system. The detection of Ab:Ag complexes in blood, and their separation and characterization, provide valuable information in the diagnosis of disease.

There are a number of techniques known for detecting and quantifying Ag, Ab, and Ab:Ag complexes, and particularly for determining the nature and amount of Ag present. These quantification techniques are called immunoassay procedures.

It has been known for some time that two naturally occurring substances, namely rheumatoid factor (RF) and a particular component of complement, Clq, have the property of combining with Ab:Ag complexes but not with either free Ag or free Ab. While there has been a prior proposal (Agnello et al., J. Exp. Med., 134, 228, 1971) to use this property in one particular way for the detection (but not the quantitative assay or absolute determination) of Ab:Ag complexes, it has never previously been recognized that RF and Clq are potentially extremely useful reagents in the analysis of Ab, Ag, and Ab:Ag complexes.

SUMMARY OF THE INVENTION

It has now been discovered that solutions of RF and Clq are in fact widely applicable reagents in analytical procedures involving Ab, Ag, and/or Ab:Ag complexes, and their use can simplify and render more accurate immunoassay procedures.

RF is a known material, and methods for its preparation and isolation are known. It is present, or can be made to appear, in the blood of a number of animal species, including man. It is normally obtained from goats or rabbits by intradermal injectons of their own purified immunoglobulins previously aggregated by heating at about 63° C. for about ten minutes. RF is then isolated from the serum obtained from the animals, by passing the serum through a column of aggregated immunoglobulins in which RF is retained. The RF can then be eluted from the column using as eluant a solution of the appropriate pH or salt concentration.

Clq is a natural circulating protein, and methods for its separation and purification are known. It is usually obtained from human, rabbit, or bovine serum by a technique known as euglobulin precipitation, which is described in J. Immunol. 106, 304–413 (1971).

In its broadest aspect, the present invention provides a method of analyzing a biological fluid sample for Ab, Ag, or Ab:Ag complexes therein which includes the step of adding to the sample, before or after adding other reagents, a solution of RF or Clq to bind with Ab:Ag complexes present therein.

There are a number of ways of carrying out this method, including the following preferred procedures:

A. Analyzing for an Ab or Ag in a biological fluid sample comprising the steps of:
   (a) adding to the sample an excess of an Ag or Ab which is specific to the unknown Ab or Ag in the sample to form an Ab:Ag complex;
   (b) adding to the mixture of (a) a known amount of a solution of RF or Clq in excess of that required to bind with all the Ab:Ag complex present, the RF/Ab:Ag or Clq/Ab:Ag formed agglomerating in the mixture;
   (c) separating from the mixture the agglomerated RF/Ab:Ag or Clq/Ab:Ag, and
   (d) measuring the amount of Rf or Clq remaining in the mixture after step (c) or separated from the mixture in step (c), and therefrom calculating the amount of Ab or Ag present in the original sample.

Preferably, step (d) comprises:
   (i) adding to the mixture remaining after step (c) a known amount of a complex Ab':Ag' in excess of the amount required to bind with all the RF or Clq in the mixture, the complex Ab':Ag' carrying an identifying label; and
   (ii) measuring the amount of Ab':Ag' which remains free in the mixture unbound to RF or Clq. Preferably, in this procedure, the identifying label is an enzyme or coenzyme such that the activity of the enzyme or coenzyme is inhibited upon binding of the Ab':Ag' complex to RF or Clq, and the amount of free Ab':Ag' is determined by measuring the enzyme or coenzyme activity of the mixture without first removing the RF/Ab':Ag' or Clq/Ab':Ag'.

B. Assaying an Ab:Ag complex in a biological fluid sample, comprising:
   (a) adding to the sample a known amount of a solution of RF or Clq in excess of the amount required to bind with all the Ab:Ag complex in the sample to form RF/Ab:Ag or Clq/Ab:Ag, which latter agglomerate in the mixture;
   (b) separating from the mixture the agglomerated RF/Ab:Ag or Clq/Ab:Ag; and
   (c) measuring the amount of RF or Clq remaining in the mixture after (b) or separated from the mixture in (b), and therefrom calculating the amount of Ab:Ag complex present in the original sample.

C. Assaying an Ab or Ag in a biological fluid sample, comprising the steps of:
   (a) adding to the sample an excess of Ag' or Ab' which is specific to the unknown Ab or Ag, in the sample to form an Ab:Ag' complex or Ab':Ag complex, the Ab' or Ag' carrying an identifying label;
   (b) adding to the mixture formed in (a) a solution of RF or Clq in an amount at least sufficient to bind with all the Ab:Ag' or Ab':Ag complex in the mixture; and
   (c) measuring the amount of Ab' or Ag' free in the mixture or bound to the RF or Clq, and therefrom calculating the amount of Ab or Ag present in the original sample.

D. A method of assaying an Ab:Ag complex in a biological sample which comprises the steps of:
  (a) adding to the sample a known amount of an Ab'λ:Ag complex which carries an identifying label, and a solution of RF or Clq in an amount insufficient to bind with the total amount of Ab:Ag and Ab':Ag' complexes in the mixture formed, and
  (b) measuring the amount of Ab':Ag' free in the mixture or bound to the RF or Clq and therefrom calculating the amount of Ab:Ag present in the original sample.

E. Assaying an Ab or Ag in a biological fluid sample, including the following steps:
  (a) adding to the sample an Ag or Ab which is specific to the sample Ab or Ag to form an Ab:Ag complex;
  (b) adding to the mixture from step (a) a known amount of the Ab or Ag to be determined, which amount carries an identifying label;
  (c) adding to the mixture formed in step (b) a solution of RF or Clq in an amount at least sufficient to bind with all the Ab:Ag complex in the mixture; and
  (d) measuring the amount of labeled Ab or Ag remaining free in the mixture or bound to the RF or Clq.

F. Qualitatively determining the presence in, or absence from, a biological fluid sample of an Ab:Ag complex by adding to the sample a solution of RF or Clq and a material which is caused to agglutinate on contact with RF or Clq, and detecting whether agglutination of the material occurs.

G. Determining the presence of a particular Ab or Ag in a biological fluid sample by adding to the sample an Ag or Ab which is specific to the particular Ab or Ag whose presence is to be determined, to form with any of the particular Ab or Ag present an Ab:Ag complex, and determining the presence or absence of such complex by the method of F.

H. Immunoassaying a biological fluid sample for Ab, Ag, or Ab:Ag complexes including the following steps:
  (a) adding to the sample an Ab, Ag, or an Ab:Ag complex carrying an enzyme label;
  (b) adding a solution of RF or Clq to bind with any Ab:Ag complex present; and
  (c) using the inhibitory effect of RF or Clq on the enzymic activity of any labeled Ab:Ag complex bound thereto as a basis for assaying the sample.

The general techniques involved in carrying out these procedures will be well understood by those skilled in the art, so that a detailed description thereof is unnecessary.

In the method of the present invention for the assay of Ab, Ag, and Ab:Ag complexes (e.g., methods A to E and H, above), a solution of RF or Clq is used. The RF or Clq binds with Ab:Ag complexes, but not with free Ab or free Ag. Thus, the RF and Clq effectively separate or bind up the Ab:Ag complexes, to form RF/Ag:Ab or Clq/Ag:Ab.

In certain instances, when RF/Ag:Ab or Clq/Ag:Ab are formed, they tend to agglomerate. When this happens, they can be removed by methods such as centrifuging or filtering, to leave a clear solution. This solution will contain either:
  a. RF or Clq, but no Ab:Ag complexes; or
  b. Ab:Ag complexes, but no RF or Clq,
depending upon whether there was used an excess or a deficiency of RF and Clq. In such cases, where efficient removal of RF/Ab:Ag or Clq/Ab:Ag is possible, quantitative assay is facilitated since it is merely necessary then to measure the amount of RF or Clq or Ab:Ag left in solution or removed from solution. (The RF/Ag:Ab and Clq/Ag:Ab removed can be treated with buffers to release the Ab:Ag from the RF or Clq.) This can be most conveniently achieved using materials which carry an identifying label, such as a radioactive atom, or an enzyme or coenzyme, or a fluorescent group. The use of such labels is well known for Ab, Ag, and Ab:Ag complexes, although it has never previously been proposed to label RF or Clq. Accordingly, in another aspect, the present invention includes as a reagent a solution of RF or Clq wherein the RF or Clq carries an identifying label.

Where an Ab:Ag complex carries (on either the Ab or the Ag) an enzyme label, which enzyme has a substrate of very large molecular weight, such as amylase whose substrate is starch, we have found that when the complex binds to RF or Clq, the activity of the enzyme is inhibited. Such an enzyme label may be bound to either the Ab or the Ag by the technique of Miles and Hales, Nature, 219, 186 (1968). When such inhibition occurs, it is no longer necessary in assay procedures to remove the RF/Ab:Ag or Clq/Ab:Ag from the test mixture since the overall enzymic activity of the mixture will be due only to labeled Ab or Ag which is not bound to RF or Clq. This is a very advantageous feature of the use of RF and Clq in immunoassays involving enzymic labeling. Hitherto, it has been necessary to remove the Ab:Ag complex from the test mixture before determining the enzymic activity. When RF and Clq are used, with a suitable enzymically-labeled Ab or Ag system, removal of the Ab:Ag complex is unnecessary. This simplification in procedure greatly facilitates continuous flow analysis procedures.

Solutions of RF and Clq are useful in all types of immunoassays. For example, they can be used in assays of an Ab or Ag, in which the whole of the Ab or Ag is converted to a complex Ab:Ag, or they can be used in competitive binding assays. Among the latter are processes in which insufficient RF or Clq is added to a test mixture, to bind all the Ab:Ag complex and labeled Ab:Ag complex therein. The amount of labeled complex which becomes bound to the RF or Clq, or remains unbound, is then determined from which the amount of Ab, Ag, or Ab:Ag in the original test sample can be determined. In another type of competitive binding assay, competition occurs between a labeled and an unlabeled Ag (for example) for a limited amount of Ab, the RF and Clq being used to bind the complex so formed and effectively separate it from the unbound Ag.

Solutions of RF and Clq are particularly useful in continuous flow analysis of biological fluid samples, and the invention includes such use.

Some of the procedures described above are now further described in more detail, by way of illustration only.

Competitive Binding Assay

This involves competition between two Ab:Ag complexes for a limited amount of RF or Clq. Thus, for example, if an excess of a labeled Ab:Ag complex is added to a limited amount of RF or Clq, then all the RF or Clq will become bound to the complex. If, then, in addition to the labeled complex, a serum sample is added containing unlabeled Ab:Ag complex, the labeled and unlabeled complex will compete on molar terms for the limited amount of RF or Clq. If, after equilibrium is reached, the RF or Clq is removed together with the complexes bound thereto, the presence (or the presence of a particular minimum amount) of labeled complex in the remaining solution indicates that the serum sample contained an Ab:Ag complex. This method can be operated quantitatively to measure the amount of complex in the serum sample, and it may be used for detecting the presence of a particular Ag or Ab, by establishing the presence or otherwise of an Ab:Ag complex after adding the specific Ag or Ab.

In the above procedure, the Ab:Ag bound to the RF or Clq may be removed if it is insoluble or otherwise selectively removable from the solution. On the other hand, where for example, enzymic labeling is involved and there is inhibition of enzymic activity on binding to RF or Clq, the bound Ab:Ag need not be removed.

Detection and Assay of Antigen

An antigen, such as morphine, can be detected and assayed as follows. Morphine is labeled with an enzyme, e.g., amylase. Specific anti-morphine antibodies, Ab" are prepared. The sample (of serum or urine, for example) to be tested for morphine, is mixed with the Ab". There is then added the enzyme-labeled morphine. This will only be able to complex with the Ab" in proportion to the concentration of morphine in the serum or urine. A solution of RF or Clq is then added.

The RF or Clq binds with the complexes formed between Ab" and the morphine (if any) in the serum and the labeled morphine, and forms agglomerates. As a result, the Ab": labeled morphine complexes so bound lose their enzymatic activity and it is then simply necessary to measure the enzymatic activity of free labeled morphine in the solution. If desired, the agglomerated RF/Ab": morphine complexes can be removed from the solution although this is not essential. A similar procedure may be used for other antigens and, mutatis mutandis for antibodies.

This procedure illustrates a very useful feature of the use of solutions of RF and Clq, namely that when they bind to Ab:Ag complexes in which the Ab or Ag is labeled with certain enzymes, agglomeration occurs with the result that the activity of the enzyme is inhibited.

General Immunoassay Procedure

It is often desirable to be able to measure the amount of an Ab, Ag, or Ab:Ag complex present in a sample liquid, and there are known techniques (immunoassay procedure) which enable this to be done. We have found that RF and Clq can be used in immunoassay procedures to advantage either in simplifying the overall procedure or in ensuring greater certainty and accuracy in the results.

We give below one general example of the use of a solution of RF or Clq in an immunoassay procedure, but it must be understood that RF and Clq can with advantage be used in other immunoassay procedures, as will be clear to those skilled in the art.

By way of example, in a typical known radiometric immunoassay procedure for assaying an antigen Ag, there is added to the solution of Ag, a known amount of the same Ag but which is radioactively labeled, Ag*. There is also added a known amount of the specific antibody for Ag (and Ag*), namely, Ab. Complexes are formed, Ab:Ag and Ab:Ag*, and these are separated out leaving a liquid containing Ag and Ag*. The amount of Ag* either in the separated complexes or in the liquid can be measured, and the amount of Ag originally in the sample can then be calculated.

While this known procedure is effective, it is laborious to carry out since, for every particular Ag (or Ab) to be measured, the radioactive labeled Ag* (or Ab*) must be obtained.

By using a solution of RF or Clq, this disadvantage can be overcome. For example, there is first added to the sample (containing the Ag to be determined) an excess of its specific antibody Ab. A complex, Ab:Ag, is formed. There is then added a known amount of a solution of RF or Clq, in excess of the amount required to bind with all the Ab:Ag complex. The RF/Ab:Ag formed agglutinates and can be removed, thus leaving in solution the excess RF or Clq (i.e., the original amount added less the amount which bound to the Ab:Ag complex). This remaining excess can then be measured, allowing one to calculate the amount of Ag originally in the sample.

The excess RF (or Clq) may be measured, for example, by using labeled RF or Clq, or by adding to it a known and excess amount of a labeled Ag':Ab' complex, e.g., one made from catalase (which is an antigen) and anti-catalase serum. The RF in solution binds to the labeled complex Ag':Ab' and the amount of RF therein can then be calculated, e.g., by measuring the enzymatic activity of the solution, optionally after removal of the complex. It may not be essential to remove the complex since, while the enzyme catalase is large relative to the Ab and will suffer no loss of activity on forming the complex Ab:Ag, it may lose activity when the complex becomes bound to RF or Clq and agglomeration occurs.

It will be appreciated that, in the above procedure using RF or Clq, apart from the specific antibody Ab, all the reagents are standard, i.e., the RF and the labeled complex Ab':Ag'. These reagents can be used for the quantitative analysis of any Ag, or (mutatis mutandis) Ab, or complex itself. (When analyzing for the complex itself, the initial step described above of adding the antibody Ab, is omitted.)

Characterization

It will be understood that many of the procedures outlined above involving the use of a solution of RF or Clq, are useful preliminaries in the characterization of Ab, Ag, or Ab:Ag complexes. Some of the procedures do directly result in identification of a particular Ab or Ag, for example, those procedures where the presence of a particular Ab is suspected and subsequently confirmed by adding the specific Ag and detecting the presence of the Ab:Ag complex.

RF and Clq are very useful reagents in the characterization of Ab, Ag, and Ab:Ag complexes, as will be clear from the foregoing description.

Identification (i.e., characterization) of an antigen is generally effected by various procedures, e.g., spectrophotometry to detect the presence of nucleic acids, electron microscopy to identify viruses, immunofluorescence with specific antisera directed against virus or tissue antigens.

For certain purposes, it may be convenient to label RF or Clq (soluble or in their insolubilized form). This can be effected with, for example, $I^{125}$ or fluorescent or coenzyme labeling (e.g., NADH).

Solutions of RF and Clq combine not only with Ab:Ag complexes but also with aggregated immunoglobulins. This fact should, of course, be borne in mind when carrying out the procedures described above, as will be clear to those skilled in the art. Aggregated immunoglobulins can be labeled, such as with radioactive iodine or a fluorochrome, and as such can be used in place of labeled Ab:Ag complexes in the analytical procedures described above, e.g., in the analysis procedure in place of the labeled Ab':Ag' complex.

Inhibition of Agglutination

RF and Clq both cause agglutination of red blood cells. Also, they will cause agglutination of materials which, for example, have a coating or outer surface of immunoglobulins, such as polystyrene particles coated with immunoglobulins. Such coatings can be formed by immunological reactions between Ab and membrane antigens, or by physical adsorption or chemical reaction. Polystyrene particles coated with immunoglobulins are commercially available but can, in any event, easily be prepared.

When such coated particles or red blood cells contact RF or Clq, agglutination begins to occur, but if there is also present in solution an Ab:Ag complex, this will react with the RF or Clq relatively quicker and the RF and Clq will become bound to the Ab:Ag complex in solution and, as a result, no agglutination of the coated particles (or red blood cells) will occur. Thus, the presence of Ab:Ag complexes in serum, for example, can be detected by contacting the serum with (soluble) RF and Clq and with particles coated with immunoglobulins. If agglutination is observed, the serum does not contain any Ab:Ag complexes.

This is a very simple and accurate test, and is applicable to the detection of all Ab:Ag complexes. An example of the procedure is as follows:

50 μl of serum are added to 50 μl of a solution of soluble Clq or RF, and the mixture is combined with 50 μl of a suspension of polystyrene particles coated with immunoglobulins. Any resulting agglutination of the particles can readily be observed.

The above test can also be used for detecting the presence of a particular Ag or Ab in serum. For example, when testing for a particular antigen, Ag', there is added to the serum the appropriate specific antibody Ab', and then the test is made for the presence of an Ab:Ag complex, namely, Ab':Ag'. If the serum originally contains other Ab:Ag complexes, these must first be removed, for example, using insolubilized RF or Clq as described in our copending application Ser. No. 578,698.

DETAILED DESCRIPTION OF THE INVENTION

In order that the invention may be more fully understood, the following Examples are given by way of illustration only.

Inhibition of RF or Clq Agglutination for Proteins

This technique relies on the power of RF or Clq of complement to bind together antigen/antibody complexes which have already been formed or latex particles to which IgG is absorbed. RF and Clq will not bind free antigen, antibody or IgG.

EXAMPLE I

In this method, sample containing the antigen is mixed with antibody, incubated, and then mixed with an excess of RF. RF is used up in proportion to the number of antigen/antibody complexes formed. Latex particles with absorbed IgG are mixed with the above mixture. The excess RF present agglutinates latex particles in direct proportion to the RF concentration. The remaining latex particles are counted in a special cell counter, with a double threshold. Thus, the more antigen originally present, the larger the numbers of antigen/antibody complexes formed. These complexes will consume more RF; as the concentration of RF is less, fewer latex particles will be agglutinated. The higher the concentration of latex monomers, the higher the original concentration of antigen.

In this and the following examples, the RF was prepared as follows:

IgG was isolated from normal human serum by DEAE Sephadex chromatography and was insolubilized by conjugation to aminated Sepharose-4B by means of glutaraldehyde (Cambiaso et al., Immunochemistry 12, 273, 1975) at a ratio of 10 mg IgG/ml. packed beads. After adsorption of RF and washing with 1M saline, RF was eluted by 0.75 molar ammonium thiocyanate and used after dialysis against 0.9% saline.

The reagent was prepared from RF solution containing 100 mg IgM/ml. of saline, latex IgG, and 0.2M glycine.

The IgG of normal pooled serum was aggregated by heating to 63° C. for 10 minutes. It was then diluted in saline 1:5 and heated for 30 minutes at 56° C. to destroy the complement Clq.

Using human RF, the response curve (inhibition) obtained on a Technicon Autoanalyzer shown at FIG. 1 showed considerably more sensitivity than that for Clq shown at FIG. 2. Inasmuch as the IgG was aggregated, it was not possible to convert these figures to molar sensitivity.

EXAMPLE II

Particle counting of monomers was successfully applied to lactoferrin in serum as follows:

Twenty microliters of serum and 20 microliters of goat anti-LF serum diluted 1:80 with 4% polyethylene glycol were incubated for 15 minutes at 37° C. Twenty microliters of this mixture were then added to 20 microliters of a solution containing 60 nanograms of RF.

Curves shown in FIG. 3 were obtained. These curves have not been investigated further, but these curves suggest that standard curves between 100 pg/ml. and 1,000 pg/ml. are possible. Assuming a molecular weight for lactoferrin of 75,000, this response suggests a sensitivity for the method of $10^{-15}$ molar.

The multiple "standard curves" apparently exhibited by RF is in keeping with the findings of Larhuma et al. (to be published) that both RF and Clq aggregations are favored by precise limits of antigen excess. For example, in the case of $(IgG_3)_n$ aggregates, RF was at its maximum "efficiency" when "n" was 7 or 21.

DETAILED DESCRIPTION OF THE DRAWINGS

Figure 1:
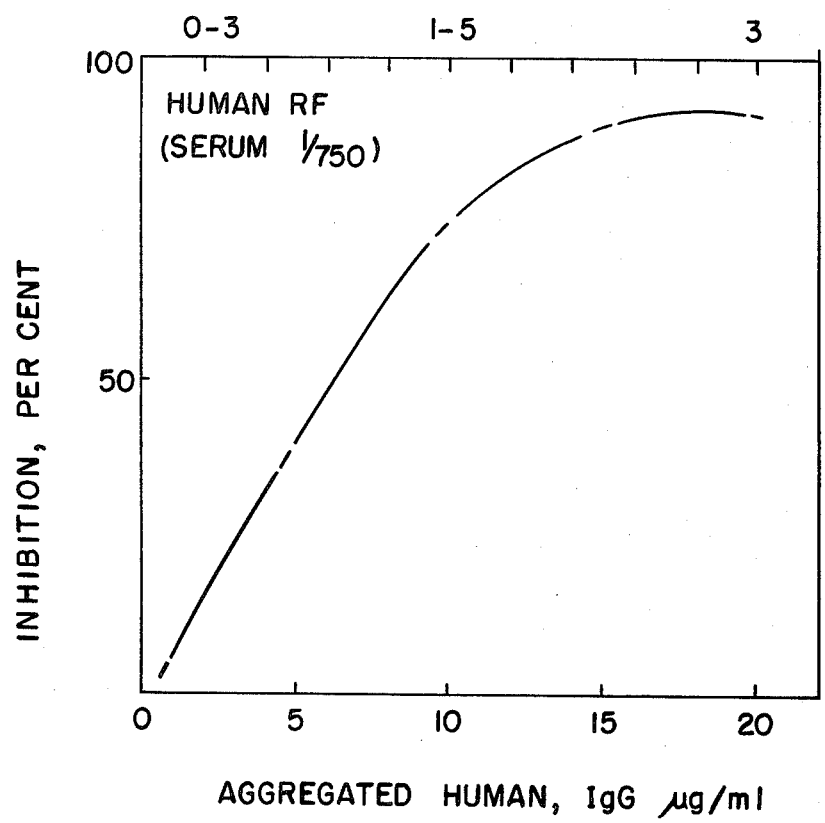
FIG. 1 illustrates the power of RF to bind latex particles to which IgG is absorbed.

FIG. 1 shows the inhibition of aggregation of human IgG by human RF, in micrograms/ml., using the technique as described in Example I.

Figure 2:
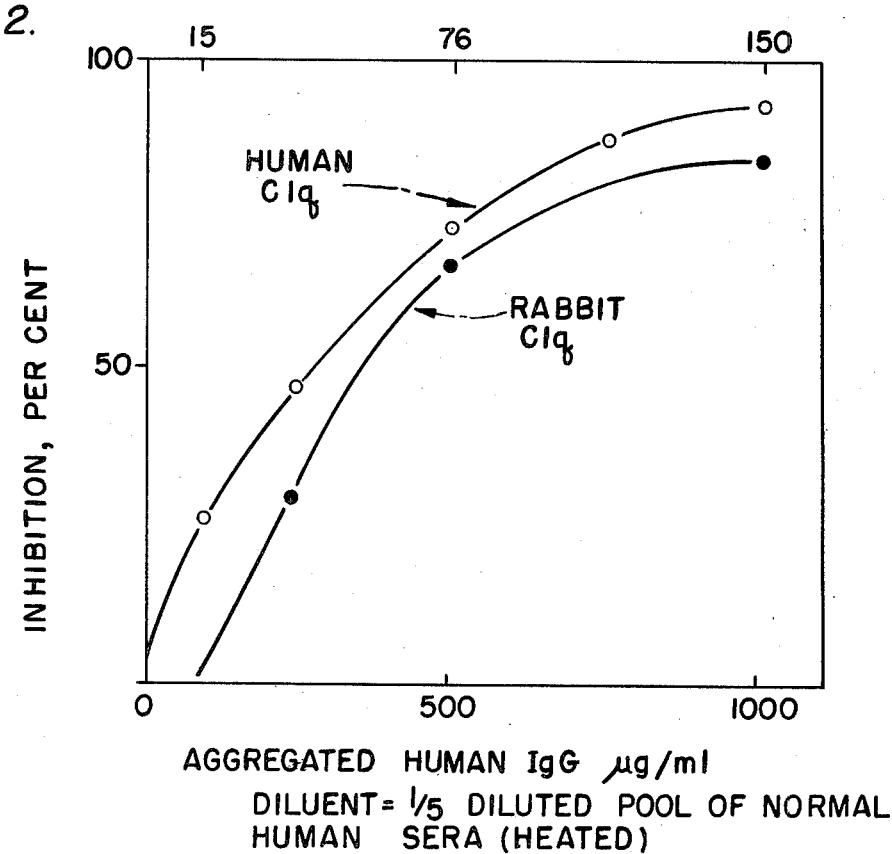
FIG. 2 illustrates the power of Clq to bind latex particles to which IgG is absorbed.

FIG. 2 shows the inhibition of aggregation of human IgG by human Clq and by rabbit Clq, in micrograms/ml., according to Example I. It should be noted that the response curve for Clq shows considerably less sensitivity than that for RF.

Figure 3B:
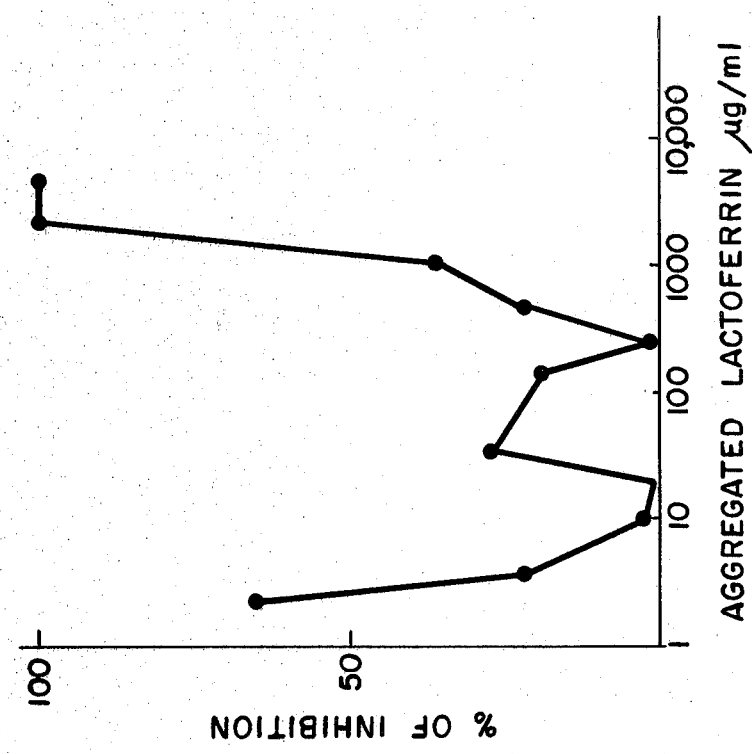
FIGS. 3A and 3B illustrate the standard curves obtained in analyses of lactoferrin using RF as a reagent.
Figure 3A:
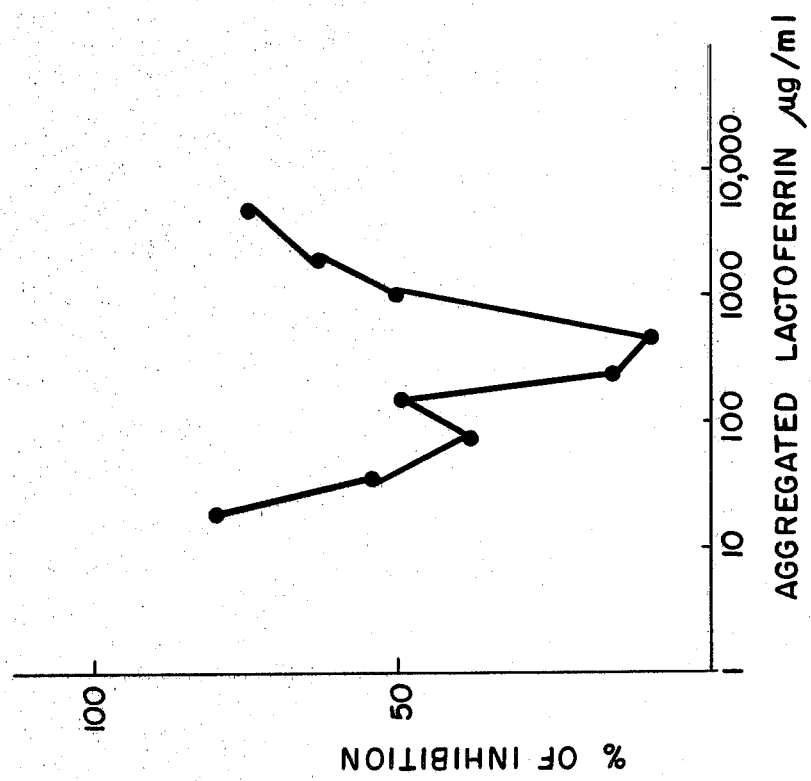

FIGS. 3A and 3B show response curves obtained in analyses of lactoferrin according to the method of Example II.

Figure 4:
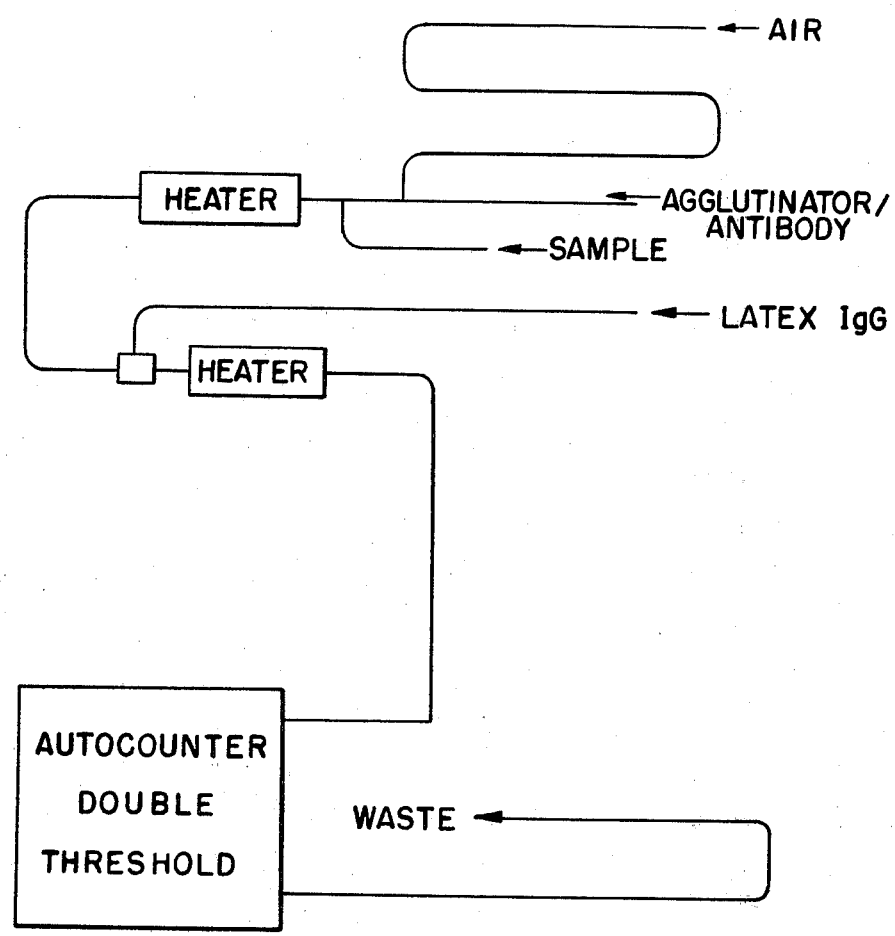
FIG. 4 is a flow diagram for the determination of lactoferrin using RF in an automated particle counting system.

FIG. 4 is a flow diagram for automated particle counting of antibodies or antigens according to the present invention. Sample containing the antigen (or antibody) to be analyzed is introduced into the apparatus. Antibody (or antigen) plus an excess of agglutinator (RF or Clq) are then introduced into the apparatus and the components are incubated in a heating zone. The agglutinator is used up in proportion of the number of antigen/antibody complexes formed. This mixture moves out of the heating zone, and latex particles with absorbed IgG are added to this mixture. The mixture of IgG/latex, agglutinator, antibody, and antigen are incubated in a heating zone; the excess agglutinator agglutinates IgG/latex particles in direct proportion to the agglutinator concentration. The remaining IgG/latex particles are then counted in a special cell counter with double threshold. Hence, the more antigen (or antibody) originally present, the larger are the number of antigen/antibody complexes formed. These complexes consume more agglutinator; as the concentration of agglutinator is less, the fewer latex particles will be agglutinated. The higher the concentration of latex particle monomers, the higher the original concentration of antigen (or antibody).

What is claimed is:

1. A method of determining the presence in, or absence from, a biological fluid sample of an Ab:Ag complex, which comprises adding to the sample a solution of RF or Clq and a material which is caused to agglutinate on contact with RF or Clq, and detecting whether agglutination of the material occurs.

2. A method of quantitatively determining the amount of Ab:Ag complex present in a biological fluid sample comprising adding to the sample a solution of RF or Clq and a known quantity of material which is caused to agglutinate on contact with RF or Clq, and detecting the amount of material which is not agglutinated.

3. The method of claim 2, wherein the material comprises an immunoglobulin coating on inert carrier particles.

4. The method of claim 3, wherein the particles comprise polystyrene.

5. The method of claim 2, wherein the amount of material which is not agglutinated is determined by particle counting.

6. A method of analyzing an Ab or Ag in a biological fluid sample comprising the steps of:
   a. adding to the sample an excess of an Ag or Ab which is specific to the Ab or Ag, respectively, in the sample to form an Ab:Ag complex;
   b. adding to the mixture formed in step (a) a known amount of a solution of RF or Clq in excess of that required to bind with all the said Ab:Ag complex;
   c. adding to the mixture formed in step (b) a known quantity of a material which is caused to agglutinate on contact with RF or Clq;
   d. determining the amount of material which is not agglutinated.

7. The method of claim 6, wherein the material comprises an immunoglobulin coating on inert carrier particles.

8. The method of claim 7, wherein the particles comprise polystyrene.

9. The method of claim 6, wherein the amount of material which is not agglutinated is determined by particle counting.

10. An automated method for determining the amount of an Ab or Ag in a biological fluid sample comprising the steps of:
    a. introducing the sample into an automated particle counting apparatus and adding to the sample an excess of an Ag or Ab which is specific to the Ab or Ag, respectively, in the sample to form an Ab:Ag complex;
    b. adding to the mixture formed in step (a) a known amount of a solution of RF or Clq in excess of that required to bind with all the said Ab:Ag complex;
    c. incubating the mixture formed in step (b) in a heating zone;
    d. removing the incubated mixture formed in step (c) from the heating zone and adding to the incubated mixture a known quantity of a material which is caused to agglutinate on contact with RF or Clq;
    e. incubating the mixture formed in step (d) in a heating zone;
    f. counting the number of unagglutinated particles of the material remaining in the incubated mixture formed in step (e).

11. The method of claim 10, wherein the material comprises an immunoglobulin coating on inert carrier particles.

12. The method of claim 11, wherein the particles comprise polystyrene.

* * * * *